United States Patent [19]

Troutner

[11] Patent Number: 4,596,547

[45] Date of Patent: Jun. 24, 1986

[54] VALVE APPARATUS FOR PHOTOACTIVATION PATIENT TREATMENT SYSTEM

[75] Inventor: Vernon H. Troutner, St. Petersburg, Fla.

[73] Assignee: McNeilab, Inc., Fort Washington, Pa.

[21] Appl. No.: 665,827

[22] Filed: Oct. 29, 1984

[51] Int. Cl.$^4$ ............... A61M 37/00; F16L 55/14
[52] U.S. Cl. ................................ 604/4; 251/9; 604/250
[58] Field of Search ............... 604/4, 5, 6, 33, 250; 251/4, 5, 6, 7, 8, 9, 10

[56] References Cited

U.S. PATENT DOCUMENTS

| | | | |
|---|---|---|---|
| 3,895,649 | 7/1975 | Ellis | 251/9 X |
| 4,078,583 | 3/1978 | Raghavachari | 251/9 X |
| 4,428,745 | 1/1984 | Williams | 604/6 |
| 4,496,351 | 1/1985 | Hillel | 604/250 |

*Primary Examiner*—Harland S. Skogquist
*Attorney, Agent, or Firm*—Mark A. Hofer

[57] ABSTRACT

Manually overridable servo controlled valve mechanisms for controlling the flow of fluids through a flexible tube for use in a photoactivatable reagent treatment system wherein photoactivatable reagents, in contact with patient blood cells, are irradiated extracorporeally and then returned to the patient.

5 Claims, 15 Drawing Figures

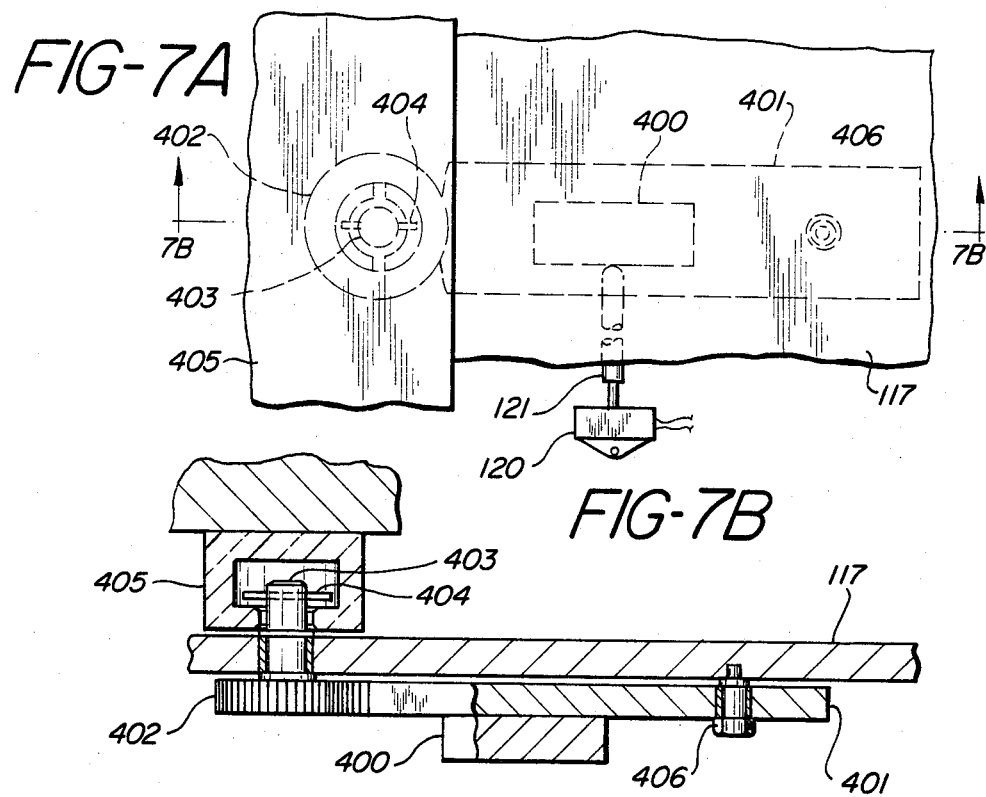
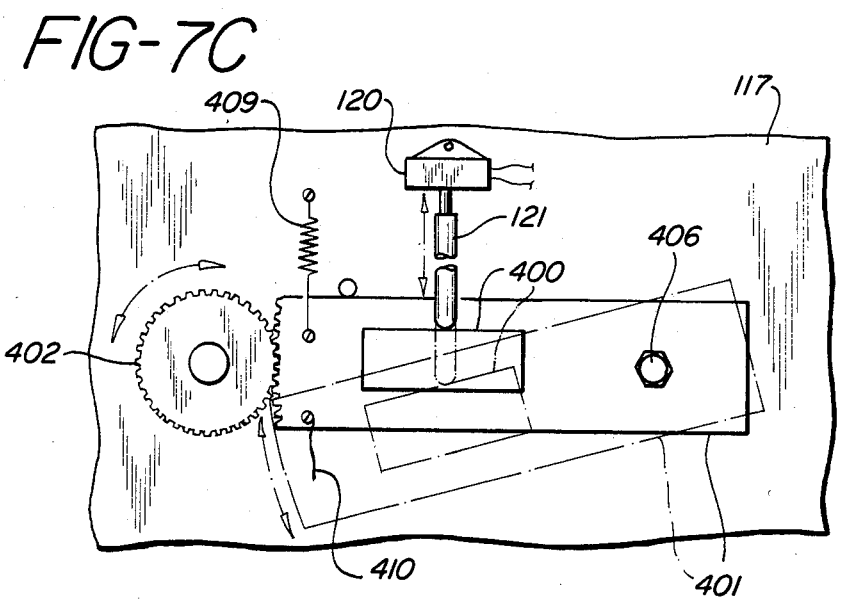

VALVE APPARATUS FOR PHOTOACTIVATION PATIENT TREATMENT SYSTEM

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation and automated, manual overridable valves therefor.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems require solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602 filed 9-17-1984 of Taylor describes a preferred form of a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to U.S. Ser. No. 650,602 filed 9-17-1984, the relevant aspects of which are fully incorporated herein by reference.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another related object to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another related object to provide a suitably automated instrument which can be monitored and operated by less trained personnel thereby lowering treatment costs in accordance with the recently enacted fiscal policies.

It is yet still another object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparent upon study of the accompanying drawings wherein:

FIGS. 7A, B and C show the centrifuge cover lock mechanism.

SUMMARY OF THE INVENTION

In accordance with the principles and objects of the present invention there are provided manually overridable, servo control valves and lock mechanisms for use with apparatus for extracorporeally photoactivating a photoactivatable reagent in contact with blood cells comprising the steps of collecting and separating on a continuous basis blood from a patient while the patient is connected to the apparatus, returning undesired blood portions obtained during separation, disconnecting the patient from the treatment system while the desired portion is photoactivatably treated whereupon the thusly treated cells are returned to the patient. Thus, the treatment system seeks to broadly maximize a patient's safety as well as optimize procedurally the various aspects of such photoactivation treatment by breaking the entire procedure down into three phases or modes. The apparatus, in the first mode, collects and separates blood on a continuous basis as it is withdrawn from the patient and to return unwanted portions to the patient all of which are accomplished while the patient remains connected to the apparatus. Thereafter, prior to energizing the irradiation sources for photoactivating the photoactivatable reagent in contact with the desired blood portion, the patient is disconnected from the machine thereby isolating him (or her) physically and electrically from the energizing high voltage, a potential source of harm. Following photoactivation, the treated cells may then be facilely returned to the patient utilizing a variety of techniques, the preferred being a simple drip chamber gravity feed infusion line.

Figure 1:
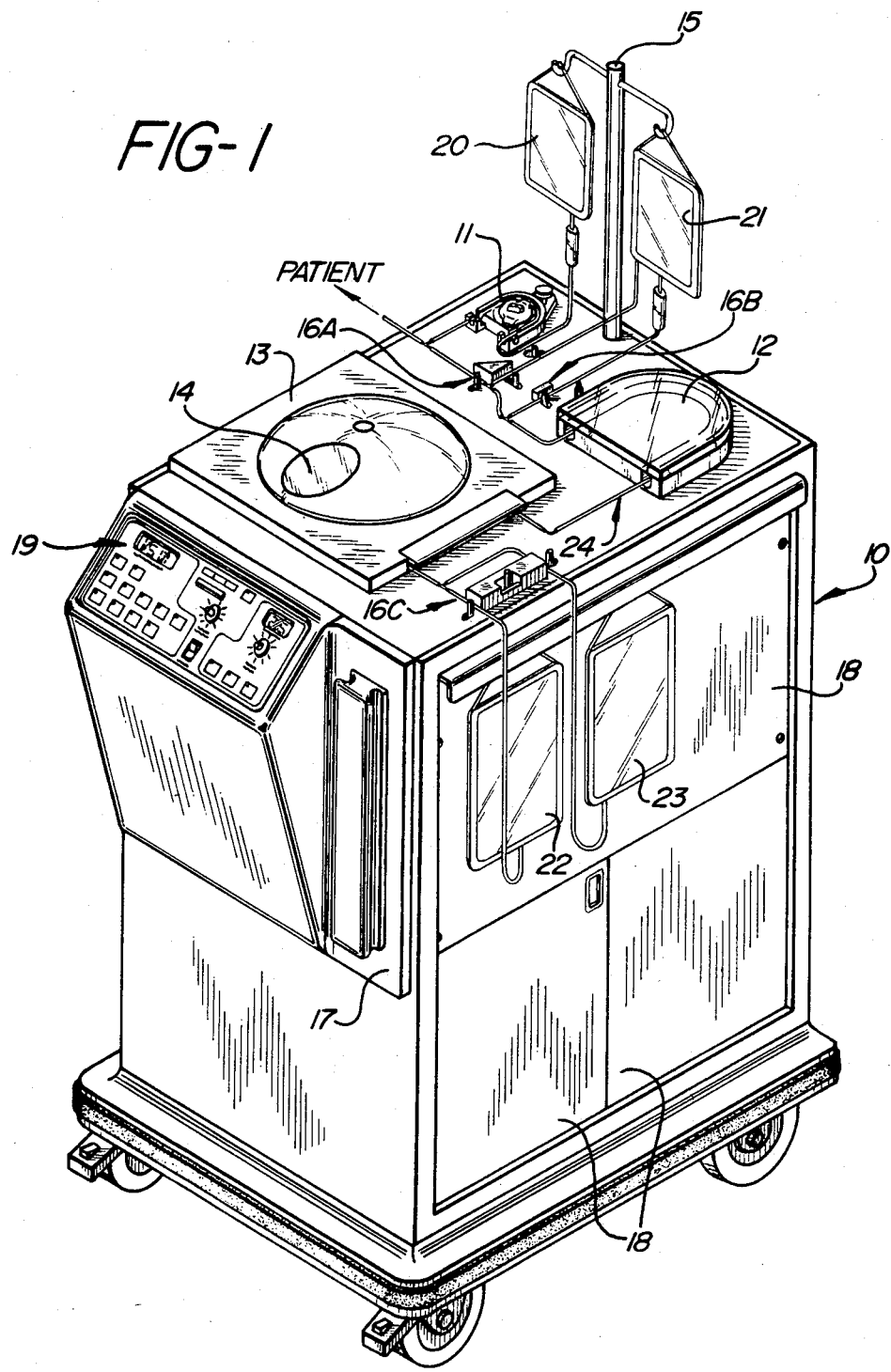
FIG. 1 illustrates a preferred configuration of the system in the collection and separation mode.
Figure 2:
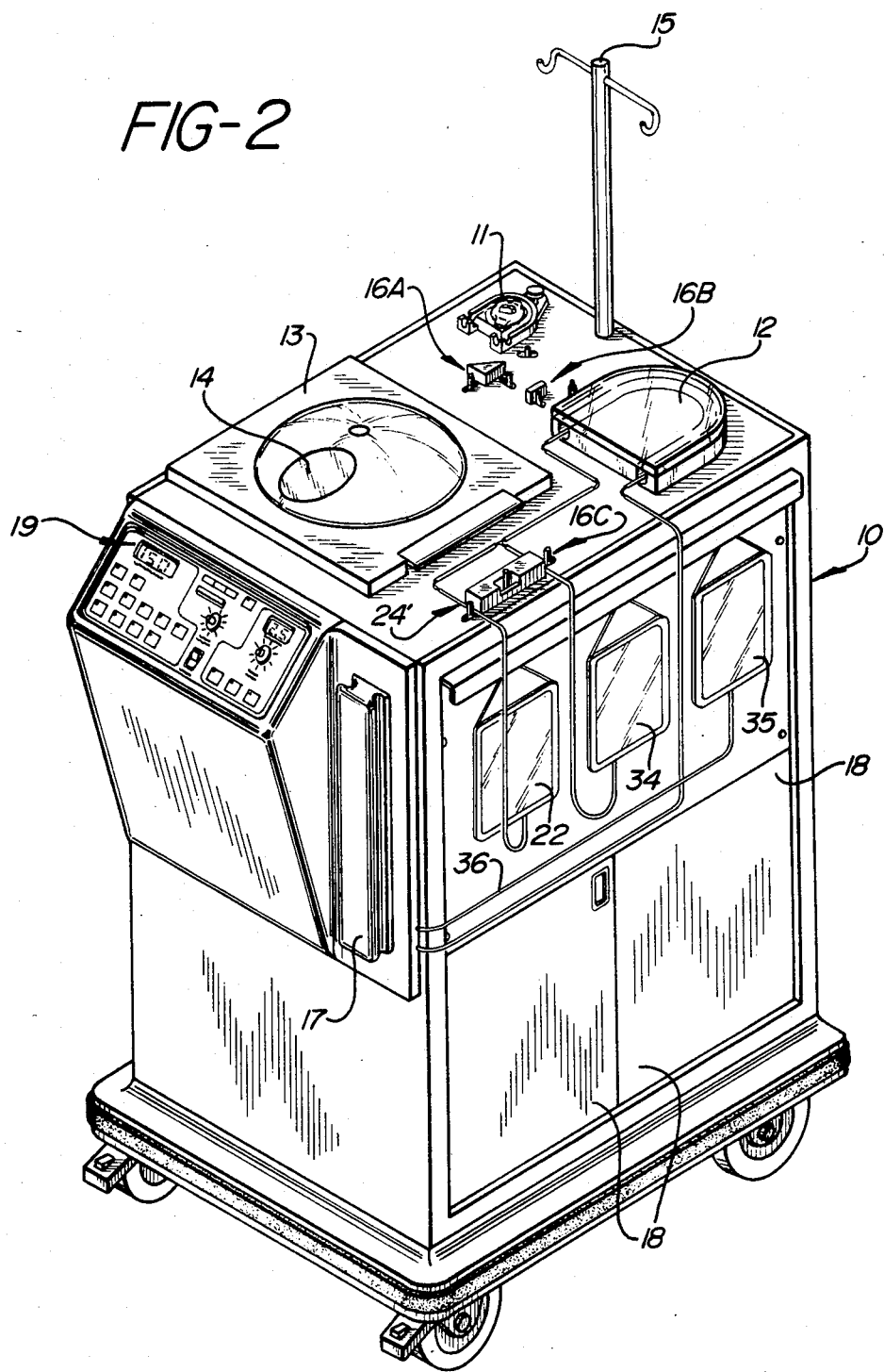
FIG. 2 depicts the system in the treatment mode.
Figure 3:
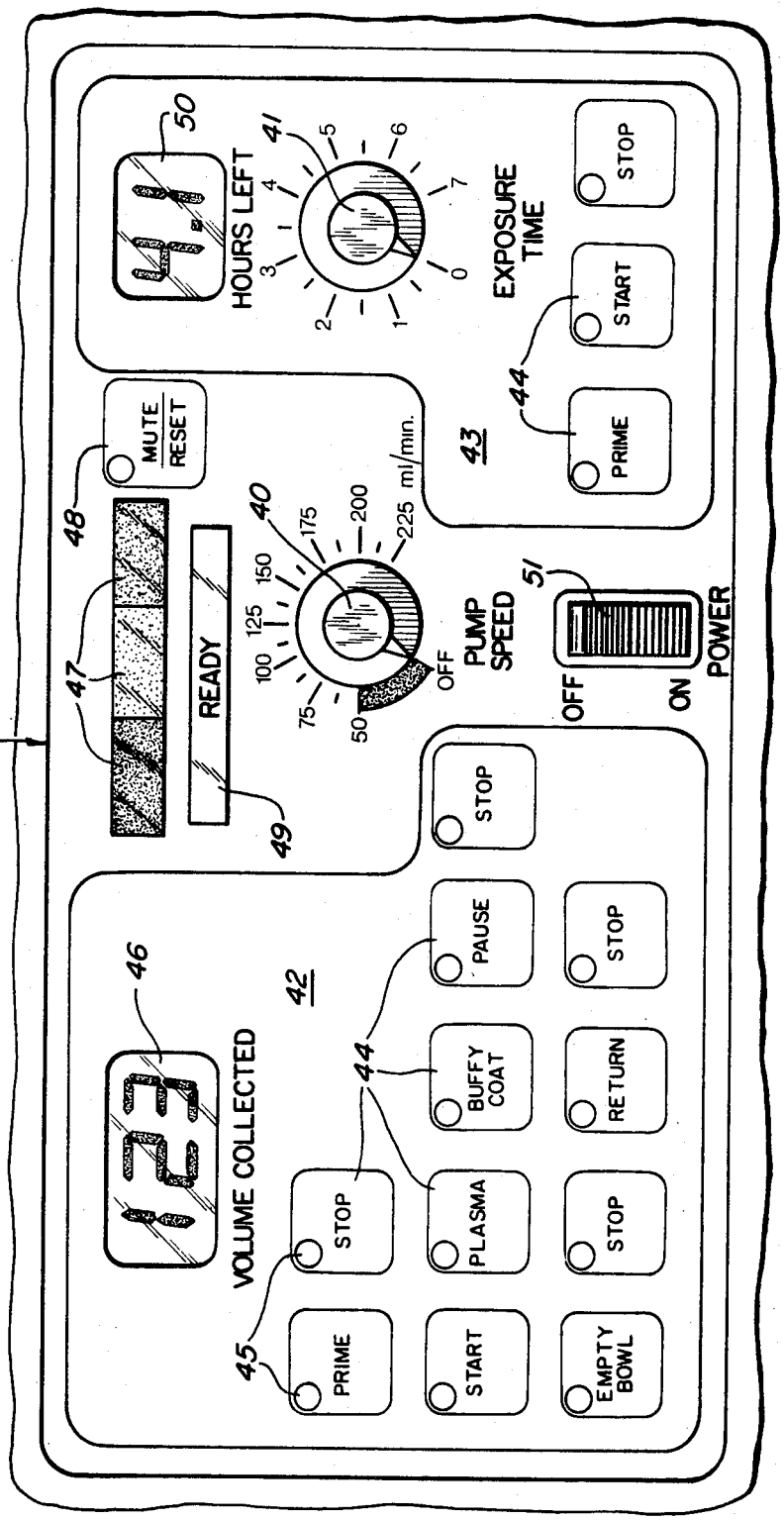
FIG. 3 shows the control panel for the system.

FIGS. 1, 2, and 3 show various aspects of the apparatus developed by the assignee hereof for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 filed 10/29/1981 to Goss entitled "Three Phase Irradiation Treatment Process"; U.S. Ser. No. 665,831 filed 10-29-1984 to King entitled "Electronic Control Methods for Puvaphoresis Apparatus"; U.S. Ser. No. 66,832 filed 8-15-1979 to King entitled "Automated Photophoresis Blood Portion Control Methods and Apparatus"; U.S. Ser. No. 665,833 filed 10/29/1984 to King et al. entitled "Patient Photophoresis Treatment Apparatus and Method"; and U.S. Ser. No. 665,817 filed 10-29-1984 to Troutner entitled "Cassette Drawer Assembly for Photoactivation Patient Treatment System", the relevant parts of which are fully incorporated herein by reference.

The operation of the device and performance of the methods can be divided into three basic phases or modes, depicted in part by FIGS. 1 and 2. The first phase is shown substantially in FIG. 1 wherein the patient is connected at the point shown, such as by veni-puncture or the like methods well-known and developed to a high degree in the dialysis arts. Patient blood, as it flows to the apparatus 10 (alternately referred to herein as the puvaphoresis apparatus or system) is preferably infused, under control of pump 11, with an anti-coagulant agent contained in container 20 hung from stand 15. Control of the flow of patient blood to the remainder of apparatus 10 is controlled largely by clamping means 16a which has the dual function of also controlling flow in the reverse direction as well as flow to return container 21; clamp 16a acting as an "or" valve.

Normally the blood flows through tubing 24 through blood pump 12 (preferably a roller pump such as that described in copending U.S. Ser. No. 636,040 filed 7/30/1984 to Troutner entitled "Improved Peristaltic Pump") into continuous centrifuge 13. This continuous centrifuge, available commercially from suppliers such as Dideco and others, is preferably capable of continuously separating blood based on the differing densities of the individual blood components. "Continuously", as used herein means that, as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through magnifying observation port 14 of the centrifuge cover, can detect qualitatively when the centrifuge emits plasma (as opposed to priming solution), leukocyte enriched portions and the remainder, i.e., nonleukocyte enriched portions, including erythrocyte enriched portions. Based on the operator's observations, he or she enters through control panel 19 (specifically via panel portion 42) the identification of the individual blood portions as they are emitted from the centrifuge. This information is entered by keys 44 (e.g. PLASMA, BUFFY COAT or leukocyte enriched portion) on control panel 19, (shown in FIG. 3) and in response thereto, the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry and the fluid contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the fluids, including erythrocytes which have been pumped into return bag 21 are gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, line 24 may be expected to contain sterilized air which is preferably removed by suitable priming operations advantageously accomplished by utilizing the anticoagulation agent in container 20; both the air and the priming solution being collected in container 23.

Also to be noted is the predetermination of the desired leukocyte enriched volumes and plasma volume to be collected within container 22 as well as the number of cycles to be employed to collect same. These volumes are selected largely in accordance with the individual volume capacities of the containers as well as the treatment cassette to be described later. Accordingly, these volumes are set in order to preferably optimize handling efficiency and to ensure patient safety. For instance, one preferred selection would include the following settings: 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions and the treatment procedure in general. Alternately, more cycles will also permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is normally required with respect to these data inputs.

Referring now to FIG. 2, a second tubing set and operating mode of the apparatus 10 is shown with the leukocyte enriched container 22 connected via tubing line 24' through valve 16c, blood pump 12 to the treatment cassette behind cassette assembly door 17 with a return line 36 to reservoir container 35. The tubing set for the second mode will also preferably include container 34 for providing a priming solution for evacuating air contained within tubing set 24' and the cassette treatment module, described in copending application of Taylor, U.S. Ser. No. 650,602 filed 9-17-1984. In brief summary, the Taylor cassette comprises a plurality of ganged cylindrical cavities each of which is concentrically mounted around a cylindrical irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the first step, PRIME, includes the pumping of priming solution from container 34 is by blood pump 12 through tubing set 24' and the treatment cassette emptying into reservoir 35. Thereafter, the operator, by pushing START in section 43, initiates actual photoirradiation treatment whereupon the leukocyte enriched portion of the blood collected within container 22, is pumped through tubing set 24' in accordance with suitably altered valve 16c through blood pump 12 to the treatment cassette and return line 36 to reservoir 35.

The treatment cassette container assembly 17 further comprises air bubble detectors for monitoring the line to and from the cassette for generating signals in response to air and which signals are conveyed to the central control means for detecting the presence of air about to enter the treatment cassette. The presence of air indicates the evacuation of container 22 and signals the end of the first treatment pass. Thereafter, the central control means reverses the direction of blood pump 12 for drawing blood from container 35 back through the treatment cassette through the blood pump and to container 22. The actual direction of the blood flow through the preferred treatment cassette is of no significance as flow in either direction is equally photoactivated. An advantage gained by reversing direction (as opposed to constant cycling in the same direction) is the increased hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then reversal thereof is continued until the desired exposure time is attained. At that point, the treated blood portion is then preferably returned to blood container 22 and the tubing set 24' may then be discarded.

Thereafter container 22 is ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, are present.

To further decrease the risk of contamination to the patient blood and blood portions, each time a connection is made or broken, it is preferably only done once. Thus, container 22 would have three connection points or ports; one for the first mode collection of the leukocyte enriched blood portion, one for the second mode treatment phase shown by FIG. 2, and the third for the third mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included in the central section are lights 47 and 49. alphanumeric display 49 indicates alarms and status regarding the machine's sequential operations. Status lights 47 are preferably provided in green, yellow, and red colors in order to provide at a glance the overall operating status of apparatus 10. Further included is a mute reset button 48 for quieting an audible alarm activated in the event an alarm condition occurs and operator input is required.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

The aforedescribed photophoresis blood treatment apparatus is made largely possible by an automated control method for directing the blood portions, derived from the continuous centrifuge, into particular containers. The automated method performs in accordance with preset volume determinations which are manually entered pursuant to a physician's direction. These predetermined volumes specify the volume to be contained within container 22 by setting forth the volume of plasma and the volume of leukocyte enriched blood portion to be directed thereto. Additionally included within these condition setting parameters is preferably the ability to set forth the number of cycles of blood collection and separation required or desired in order to obtain the desired blood volumes.

The volumes collected are determined in accordance with the blood volume pumped by the blood pump. This may be suitably monitored and communicated to the central control means by specifically monitoring the speed of the blood pump rotation. Rotation may be conveniently monitored such as by attachment of a slotted disk to the shaft and the passage of slots determined by an optical sensor means. The resultant periodic signal may be conveniently correlated with speed of rotation by circuit designs wellknown in the art. The rotational speed coupled "with the known volume pumping characteristics of the pump, will provide the necessary information regarding the volume of blood pumped. It will readily be appreciated that the sensors need not be optical buy may be electronic or mechanical instead.

In actual operation, the ideal procedure would be as follows. The operator primes the tubing set, the blood pump, and the centrifuge with the anti-coagulation solution contained in container 20. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 23. At some point, the priming solution will be completely displaced from the rotating centrifuge and plasma will begin to emerge. This emergence may be directly observed through port 14 whereupon the operator presses the PLASMA key on control panel section 42. Thereafter, the central control means automatically directs the plasma into container 22 by altering valve 16c keeping track of the volume as it does so since the volume entering the centrifuge equals the volume emerging therefrom. This continues until the operator indicates the leukocyte enriched portion, i.e. buffy coat has begun by pressing the respective data entry key in control panel section 42 whereupon, the leukocyte enriched portion continues to container 22, however, the volume so directed is monitored as buffy coat volume. Alternately, if all of the predetermined plasma volume is collected prior to the emergence of the buffy coat, then the central control means automatically diverts, by valve 16c, the emerging plasma fluid stream to container 23. In that instance, upon the emergence of the buffy coat and the keying of the BUFFY COAT data entry switch 44, the central control means diverts the emerging buffy coat into container 22 again keeping track of its volume.

The collection of the buffy coat will preferably continue in accordance with both the predetermined buffy coat volume as well as the number of cycles, also a predetermined condition by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and returning all nonleukocyte fluids, predominantly erythrocytes and perhaps excess plasma, to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the instant invention serves to automatically keep track of the volumes as they are collected thereby facilitating the institution of a convenient number of cycles whereby the removal of large blood volumes from the patient is avoided. Not only is patient safety enhanced thereby, but the automated nature of the procedure further increases safety since, in accordance with the programmed conditions supplied to the central control means, the operator need not attempt to keep track of plasma and leukocyte enriched volumes collected, while still being assured that the final solution for treatment will contain the predetermined and desirable leukocyte concentration.

Figure 5A:
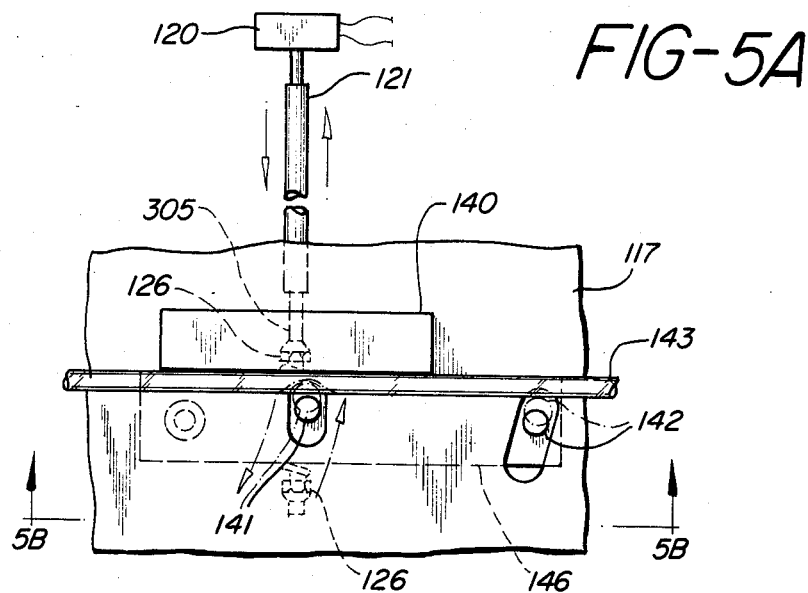
FIGS. 5A, B and C show a pivoting "on/off" valve of the present invention.
Figure 5B:
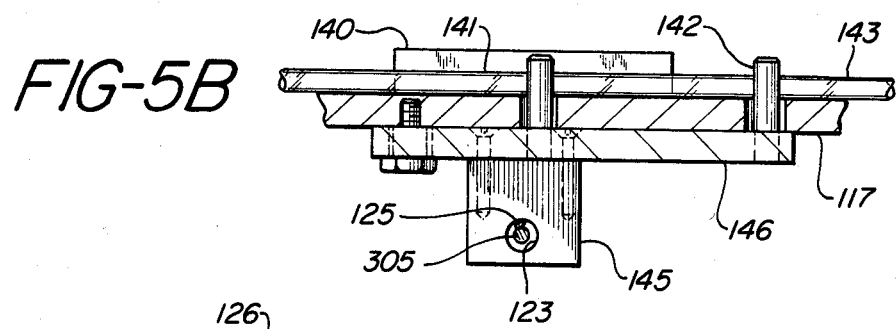
Figure 5C:
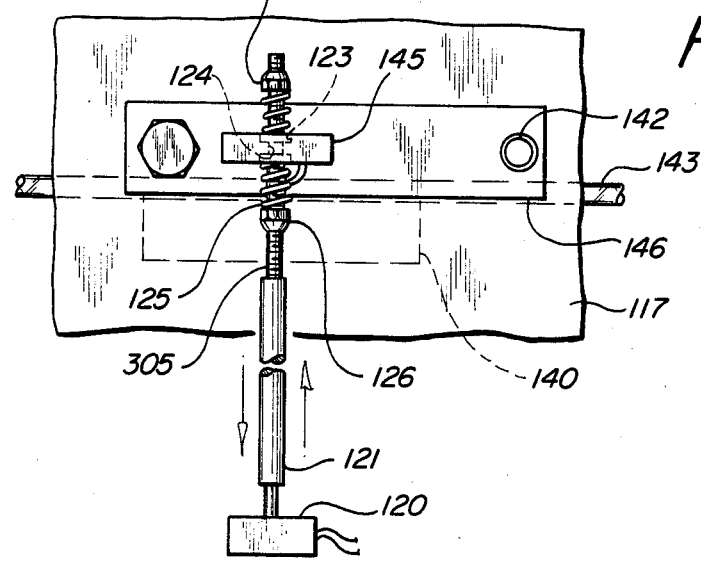
Figure 6A:
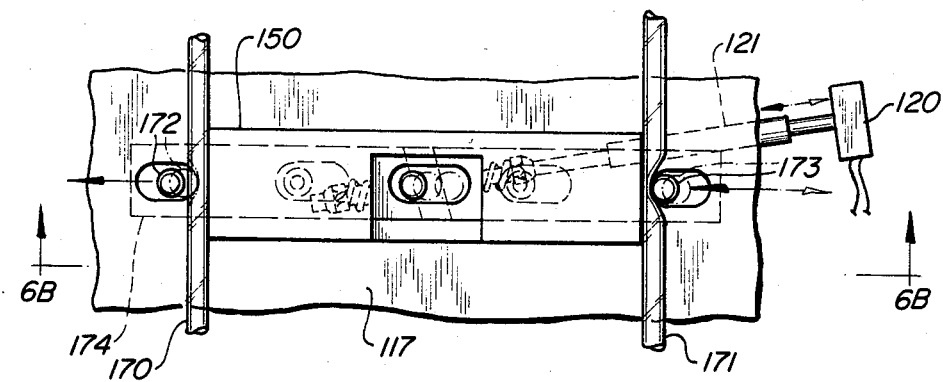
FIGS. 6A, B and C show a sliding "or" valve of the present invention.
Figure 6B:
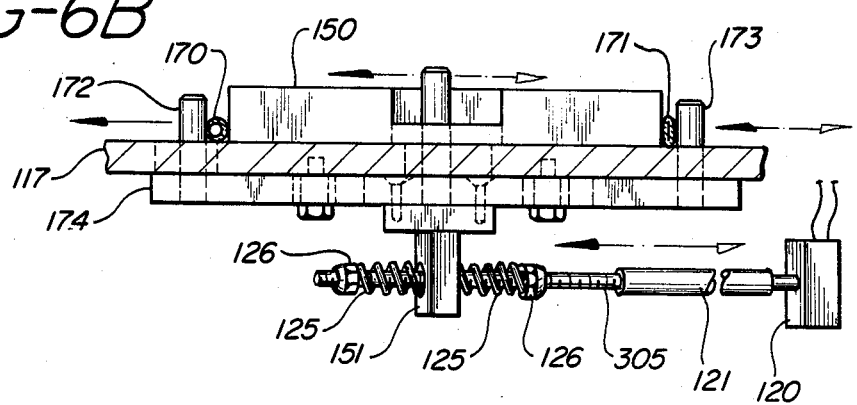
Figure 6C:
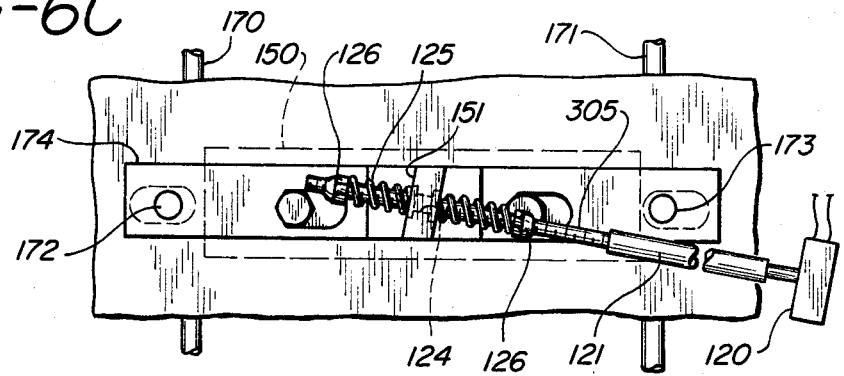

The foregoing described automated methods used in the photophoresis apparatus described with respect to FIGS. 1 and 2, depends heavily upon the instant inventions, in particular servo controlled valve mechanisms which may be manually overridden without requiring any efforts to disengage the servo control means whereby fluid flow through the tubing sets during the operational phases may be readily controlled. These mechanisms are shown in FIGS. 4, 5, and 6 which describe the valve arrangements 16a, 16b, and 16c respectively while the FIG. 7 series shows the centrifuge interlock mechanism also employing the principles of the instant invention.

Figure 4A:
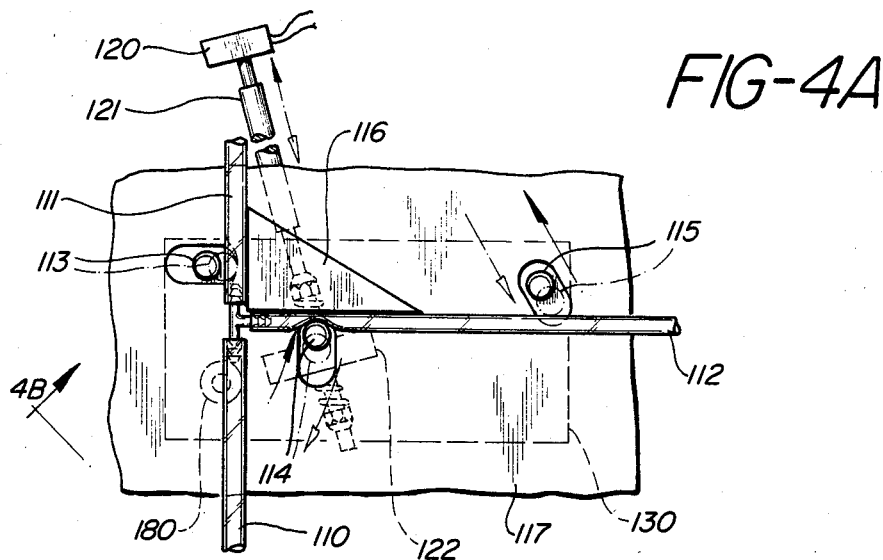
FIGS. 4A, B and C show a pivoting "or" valve of the present invention.
Figure 4B:
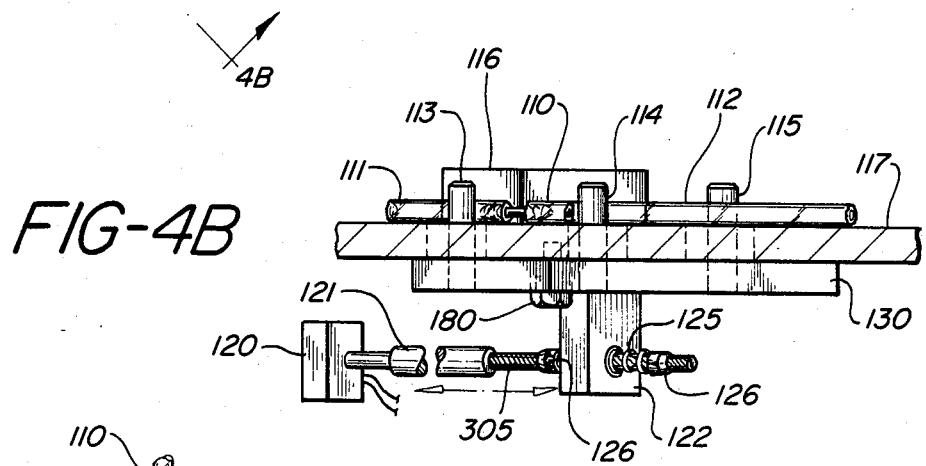

With specific reference to FIGS. 4A, B and C, depicted are top, side and bottom views of a pivoting "or" valve shown in FIG. 1 as 16a. Tubing portion 111 is connected to the patient and leads alternately to tubing 112 connected to the return container 21 (FIG. 1) and to tubing 110 which leads toward the blood pump 12 (FIG. 1). The tubing sections 111 and 112 rest against anvil means 116 which is fixedly mounted on work surface 117. Clamping pins 113 and 114 operate alternately to squeeze tubing sections 111 and 112 respectively against anvil means preferably pinching the lines into full acclusion or permitting free flow. Clamping pins 113 and 114 are mounted to motion translator 130 which pivots about pivot point 180 serving the additional purpose of retaining the motion translator 130 against the bottom of work surface 117. Further attached to motion translator 130 is handle 115 which advantageously allows the application of manual force to override servo motor 120. Work surface 117 has suitable slots cut therein to allow freedom of movement for clamping pins 113, 114 and handle means 115. The motion translator means 130 has additionally associated therewith actuator bar 121 and attachment block 122 whereby force from the servo motor 120 is translated to clamping pins 113 and 114. The actuator bar 121 has preferably a threaded portion 305 at the end thereof whereby means for engaging the threadable portion, such as lock nuts 126, can hold resilient means 125, such as a spring, against either or ideally both sides of block 122. The most preferred servo motor is a digital linear activator such as manufactured by AIRPAX, Cheshire, Conn.

Figure 4C:
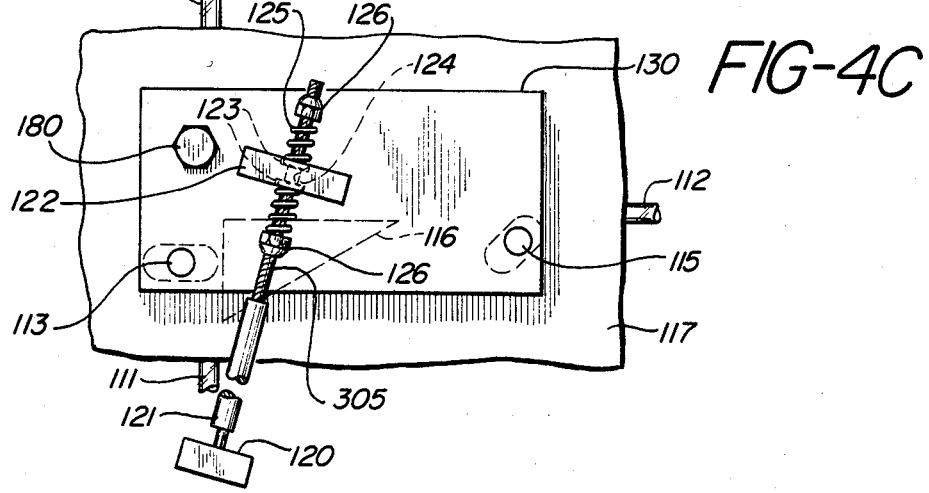

As will be noted in FIG. 4C, block 122 has a central cavity 124 of larger diameter than threaded portion 305 to allow free movement of the threaded portion therethrough. Block 122 further has in the ideal situation, cut outs 123 for receiving the end of resilient means 125 on either side of block 122. Thus, force exerted along the actuator arm 121 is translated to block 122 through resilient means 125. Lock nuts 126 allow for adjustment thereby increasing or decreasing the tension applied by resilient means 125 to block 122. Thus, the resilient means serves not only to modify the force applied against the anvil 116 by clamping pins 113 and 114 exerted by servo 122, but also serves to adjust the amount of force required to manually alter the position of motion translator means 130 by means of handle 115. By decreasing the distance between the lock nuts 126 on either side of block 122, increased spring tension is afforded against block 122 thereby translating greater force exerted by servo motor 120 and simultaneously also requiring the exertion of greater manual effort on handle 115 in order to alter the position of motion translator 130 and hence clamping pins 113 and 114.

As may be readily apparent, manual override is desirable in order to facilitate the mounting and unmounting of tubing sets during operational phase changes. Also readily apparent, is that alternate means may be used in place of lock nuts 126 for securing the ends of resilient means 125 along actuator arm 121. Threadable engaging methods are preferred inasmuch as they allow for easy adjustment potentially necessary in the event changes are made regarding the types or sizes of tubing sets employed and hence their characteristic resiliency. Stiffer tubing may require greater application of force through servo motor 120 thereby necessitating higher spring tension be applied against block 122.

FIG. series 5 shows an "on/off" valve employed as valve 16b for controlling return flow from container 21 to the patient as well as for preventing inadvertent flow into container 21. As in Figure series 4A, B and C, the servo motor 120 preferably is of identical construction as is actuator arm 121 although this need not be so. In the "on/off" valve, however, although the anvil means 140 in the FIG. 5 series is rectangularly shaped rather than triangularly shaped, as in the FIG. 4 series, clamping pin means 141 pinches line 143 against anvil block 140 in a similar manner. Force from the servo motor is translated to the motion translator 146 below work surface 117 through block 145; the threaded portion 305 passing through section 124 in the center of block 145 and held in relative juxtaposition with respect to 145 by resilient means 125 and locking nut means 126. Handle 142 protruding through work surface 117 and attached to motion translator 146 allows for manual disengagement of the clamping pin 141.

Sliding "or" valve 16c (FIG. 1) is shown in the FIG. 6 series of drawings. In this case, the anvil means 150 is again rectangularly shaped, however, with the manual override handle attached to motion translator 174 extending substantially through the center thereof. Clamping pins 172 and 173, attached to the motion translator 174, alternatively, clamp tubing sections 170 and 171 respectively against the ends of anvil means 150. As in previous drawings, an identical servo motor 120 and actuator arm 121/305 may be efficaciously employed although it should be readily apparent that other motors or actuator arm shapes may be employed. As in the previous valve devices, force from servo 120 is transmitted to motion translator 174 through block 151 by the tension produced thereagainst by resilient means 125 held in place along threaded portion 305 of actuator arm 121 by lock nuts 126.

It should be further readily apparent that the relative angles between the actuator arm and the motion translator means in the valves of FIGS. 4, 5, and 6 may be varied without departing from the invention hereof.

The manual override principle of the foregoing valves was equally applied to the generation of a centrifuge interlock mechanism for ensuring operator safety by preventing access while the centrifuge is rotating. The portion of the centrifuge cover engaging with rotatable lock means 403/404 is shown as 405. In particular, 405 may be conveniently made with the slot at the bottom thereof of suitable dimension for accepting the diameter of rotatable locking pin 403 but not permitting the passage of locking pins 404 unless the rotatable lock means is rotated to a certain position. For example, FIG. 7B shows the lock position and rotation of lock means 403 by 90° would align pins 404 with an elongated shaft opening thereby allowing cover 405 to be lifted away from work surface 117. Motion translator 401/400 is held against work surface 117 by pivot point 406. The distal (to pivot point 406) end of motion translator 401 has teeth for matable engagement with gear means 402 associated with the rotatable lock pin 403. Thus, lateral movement of motion translator 401 results in rotation of 402 and hence rotation of pin 403 causing locking pins 404 to engage or disengage with centrifuge cover 405. Force from servo 120 is transferred to motion translator 401 by actuator arm 121 which, in this case does not require a threadable portion 305, but merely butts against block 400 attached to motion translator 401. Resilient means 409 acts to ensure contact between actuator arm 121 and block 400 so that such contact may be maintained without the need for a firm attachment such as a pivot hinge. Manual override means 410 is attached to motion translator 401 for the application of manual force in a direction opposed to the force created by resilient means 409 whereby motion translator means 401 may be moved away from actuator arm 121, rotating gear 402 and hence pin 403 and locking pins 404. Thus, in the case of a power failure or other operational defect regarding the control of servo 120, the centrifuge cover may be opened in an emergency for the removal of blood components thereby allowing their return to the patient. For this reason, manual override means 410, such as a wire, string or rod, is preferably contained within apparatus 10 behind doors 18 and not provided by means of a handle pin attached to motion translator 401 and extending through work surface 117. Such a handle would provide too great an opportunity for an operator to override the safety measures provided by this invention in unwarranted circumstances. Upon study of the accompanying figures, and the foregoing description, it will become readily apparent to the skilled artisan that numerous alterations may be made to the foregoing without departing from either the spirit or scope of the instant invention.

What is claimed is:

1. Apparatus for controlling the flow of fluids through a flexible tube for use in a photoactivatable reagent treatment system comprising:

actuator means for supplying force in response to a signal;

clamping means movably mounted on a work surface;

anvil means mounted on said work surface adjacent to said clamping means whereby flow through said flexible tube, placed therebetween, may be reduced by movement of said clamping means toward said anvil means thereby compressing of said flexible tube;

motion translator means, associated with said clamping means, for moving said clamping means in response to force supplied by said actuator means;

actuator bar means having one end connected to said actuator means and the other end associated with said motion translator means for communicating said force to said motion translator means and wherein said motion translator means includes an orifice for slidably receiving said actuator bar, said actuator bar further including resilient means on both sides of said orifice whereby said force is translated to said motion translator means through said resilient means and whereby the position of said clamping means may be manually altered without activation of said activator means.

2. The apparatus of claim 1 wherein the end of said actuator bar associated with said motion translator means is adapted to receive in threadable engagement therewith nut means for securing the end of said resilient means not associated with said motion translator means whereby the compressive force exacted by said resilient means against said motion translator means may be adjusted.

3. The apparatus of claim 2 wherein said clamping means includes at least two clamping pin means which move towards and away from said anvil means to cooperate to control the fluids through two flexible tubes, placed between said clamping means and said anvil means, in an "or" configuration.

4. The apparatus of claim 3 wherein said anvil means has two surfaces meeting at an angle less than 180° and said clamping means includes two clamping pin means with a pivot point therebetween whereby one clamping pin means manually compresses one flexible tube against one anvil surface while the other tube is not compressed and upon the application of force from said actuator means said clamped tube is released and said unclamped tube is compressed.

5. The apparatus of claim 3 wherein said anvil means includes two parallel surfaces and at least two clamping pin means which slide perpendicularly to said parallel surfaces whereby a flexible tube passing between each of said clamping means and said parallel surfaces may be compressed against said surfaces, said clamping means moving concomitantly upon the application of force from said actuator means whereby one clamping pin means normally compresses one flexible tube against one parallel surface while the other tube is not compressed and upon the application of force from said actuator means, said clamped tube is released and said unclamped tube is compressed.

* * * * *